United States Patent
Li et al.

(10) Patent No.: US 7,108,718 B1
(45) Date of Patent: Sep. 19, 2006

(54) GOLD EYELID WEIGHT IMPLANT

(76) Inventors: Philip Shihua Li, 239-56 66th Ave., Douglaston, NY (US) 11362; Erik Melling, 1641 North St., Philadelphia, PA (US) 19130

( * ) Notice: Subject to any disclaimer, the term of this patent is extended or adjusted under 35 U.S.C. 154(b) by 0 days.

(21) Appl. No.: 10/889,581

(22) Filed: Jul. 12, 2004

(51) Int. Cl.
  *A61F 2/14* (2006.01)
  *A61F 2/00* (2006.01)
(52) U.S. Cl. ............. 623/4.1; 623/11.11; 424/427
(58) Field of Classification Search ........... 623/4.1, 623/11.11; 424/427
  See application file for complete search history.

(56) References Cited

U.S. PATENT DOCUMENTS

| | | | |
|---|---|---|---|
| 4,595,713 A | 6/1986 | St. John | |
| 5,137,728 A | 8/1992 | Bawa | |
| 5,164,188 A | 11/1992 | Wong | |
| 5,542,437 A * | 8/1996 | Blackmore et al. | 128/899 |
| 6,482,428 B1 * | 11/2002 | Li et al. | 424/427 |

\* cited by examiner

*Primary Examiner*—David J. Isabella
(74) *Attorney, Agent, or Firm*—Michael I. Kroll

(57) ABSTRACT

An eyelid implant for implanting in an upper eyelid of a person having a main body with a water-drop shape. The main body has a head end with a center of gravity at substantially a center point thereof, and a tail end. The diameter of the head end is greater than a diameter of the tail end. At least one suture hole extends completely through the main body. At least one suture channel extends partially through the main body to a predetermined depth. A suture is passed through the at least one suture hole for securing the eyelid implant to an eyelid of a user and said implant causes said eyelid to close.

11 Claims, 7 Drawing Sheets

GOLD EYELID WEIGHT IMPLANT

BACKGROUND OF THE INVENTION

1. Field of the Invention

The present invention relates generally to implants and, more specifically, to a gold weight eyelid implant that is shaped to conform substantially to the cornea and the eyeball in order to achieve an optimum center of gravity for maximum efficiency in aiding closure of the eyelid as well as an unobtrusive cosmetic result.

2. Description of the Prior Art

There are other gold eyelid weights designed for implantation. Gold eyelid weights are well known in the art and are used for the treatment and functional rehabilitation of patients with deficient eyelid closure or ocular exposure, a complication often caused by facial nerve palsy. The implantation of gold eyelid weights in patient's eyelids has proven to be a safe, effective means for utilizing gravity to assist in satisfactory eye closure and partial recreation of a natural eye blink reflex.

There are, however, downsides in conventional gold eyelid weights known in the art, specifically the typical rectangular shape and uniform thickness thereof. The gold eyelid weight and eyelid travel adjacent the cornea, a bulbous projection emanating from the eyeball. A rectangular gold eyelid weight has a center of gravity close to the upper surface of the cornea and the eyeball thereby requiring a larger size gold eyelid weight to offset the center of gravity and accomplish full lid closure. Unfortunately, these larger size gold eyelid weights are prominently visible beneath the upper eyelid skin and are cosmetically undesirable.

Numerous types of eyelid implants have been provided in the prior art. For example U.S. Pat. Nos. 5,137,728, 4,595,713, 5,164,188 and 6,482,428 all are illustrative of such prior art. While these units may be suitable for the particular purpose to which they address, they would not be as suitable for the purposes of the present invention as heretofore described.

U.S. Pat. No. 5,137,728

Inventor: Rajan Bawa

Issued: Aug. 11, 1992

An ocular insert for insertion into the cul de sac of the eye which is a substantially circular disc having a concave posterior surface and a convex anterior surface with a radius of curvature less than that of the sclera and a center thickness of less than about 1.5 mm U.S. Pat. No. 4,595,713

Inventor: Kenneth St. John

Issued: Jun. 17, 1986

A medical implant useful in the regeneration of soft and hard connective tissue, such as cartilage and bone, is disclosed which comprises a copolymer of a major amount of epsilon caprolactone and a minor amount of lactide. Where regeneration of bone tissue, in particular, is desired, the copolymer may further include osteogenic material in powdered or particulate form. If soft tissue regeneration is desired, the copolymer may include chopped carbon fiber. A mass of the copolymer, optionally including additives, may be molded by hand by heating the polymer to a temperature of 115.degree.–160.degree. F., by, for example, immersion in hot water. The mass is then molded to the void to be filled or shape the regenerated tissue is desired to assume, and implanted in the patient. The mass is gradually U.S. Pat. No. 5,164,188

Inventor: Vernon G. Wong

Issued: Nov. 17, 1992

Encapsulated agents are employed for introduction into the suprachoid of an eye for therapeutic purposes. The administration of drugs is controlled and maintained for long periods of time, while ensuring the substantial absence of significant levels outside the site of administration. While these gold eyelid weights may be suitable for the purposes for which they were designed, they would not be as suitable for the purposes of the present invention, as hereinafter described.

U.S. Pat. No. 6,482,428

Inventor: Li et al.

Issued: Nov. 19, 2002

A weighted upper eyelid implants for assisting and achieving complete eyelid closure and partial recreation of a natural blinking reflex. The implant is formed of a main plate having suture channels extending partially therethrough for receiving a suture knot tied in a suture passing through an adjacent suture hole thereby securing the weighted implant to the eyelid while preserving a cosmetically pleasing image.

SUMMARY OF THE PRESENT INVENTION

The present invention relates generally to implants and, more specifically, to a gold weight eyelid implant that is shaped to conform substantially to the cornea and the eyeball in order to achieve an optimum center of gravity for maximum efficiency in aiding closure of the eyelid as well as an unobtrusive cosmetic result.

A primary object of the present invention is to provide a gold eyelid weight that overcomes the shortcomings of the prior art.

Another object of the present invention is to provide a gold eyelid weight having an arcuate waterdrop-shape in cross section designed to create a center of gravity positioned in a manner to best utilize the gravitational pull thereupon.

Another object of the present invention is to provide a gold eyelid weight wherein the head thereof is substantially thicker and wider than the tip of the tail portion thereby concentrating the mass of the device therein.

Yet another object of the present invention is to provide a gold eyelid weight wherein the tail portion thereof is dynamically thin and lies unobtrusively above the eyeball.

Still yet another object of the present invention is to provide a gold eyelid weight that when shown in cross section tapers gradually as it follows the curvature of the eyeball from the center to the top.

Yet another object of the present invention is to provide a gold eyelid weight that requires less weight and size to work as effectively as other gold eyelid weights known in the art.

Still another object of the present invention is to provide a gold eyelid weight that is less visible when implanted than conventional gold eyelid weights.

Another object of the present invention is to provide a gold eyelid weight that is inexpensive to manufacture.

Yet another object of the present invention is to provide a gold eyelid weight that is simple and easy to use.

The present invention seeks to overcome the shortcomings of the prior art by providing a gold eyelid weight that is waterdrop-shaped in profile to substantially conform to the curvature of the cornea and eyeball. The front portion of the gold eyelid weight of the present invention is thick and represents the majority of the weight thereof as it tapers dramatically towards the tail. This unique design shifts the load to the front which moves forward and downward in an arcuate manner more effectively than the prior art due to the forwardly positioned center of gravity. The gold eyelid weight of the present invention provides enhanced utilization of gravitational force thereby requiring a smaller and lighter gold eyelid weight to achieve the same results as the bulkier gold eyelid weights known in the art.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
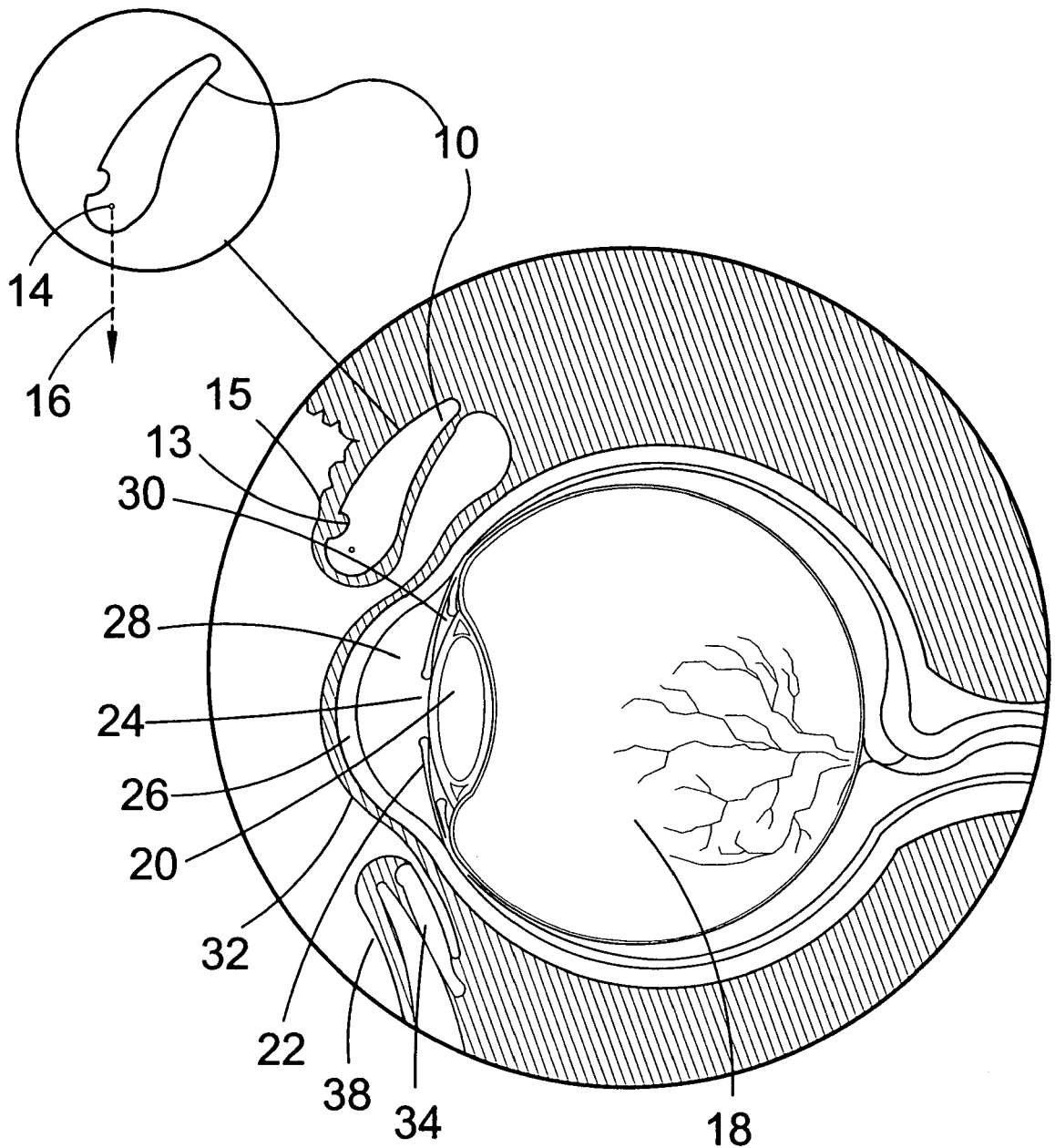
FIG. 1 is sectional view of the eyelid implant of the present invention in use.

Turning now descriptively to the drawings, in which similar reference characters denote similar elements throughout the several views, the Figures illustrate the eyelid implant having suture channels of the present invention. With regard to the reference numerals used, the following numbering is used throughout the various drawing figures.

| | |
|---|---|
| 9 | front side |
| 10 | eyelid implant of the present invention |
| 11 | main body of the implant |
| 12 | suture hole |
| 13 | suture channel |
| 14 | gravity point |
| 15 | upper eyelid |
| 16 | direction arrow |
| 17 | back side |
| 18 | vitreous body |
| 20 | lens |
| 22 | iris |
| 24 | pupil |
| 26 | cornea |
| 28 | anterior chamber |
| 30 | posterior chamber |
| 32 | conjunctiva |
| 34 | ciliary body |
| 36 | open position |
| 38 | lower eyelid |
| 40 | closed position |

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments. Practitioners skilled in the art will recognize numerous other embodiments as well. For definition of the complete scope of the invention, the reader is directed to appended claims.

Turning now descriptively to the drawings, in which similar reference characters denote similar elements throughout the several views, FIGS. 1 through 7 illustrate the eyelid implant of the present invention indicated generally by the numeral 10.

FIG. 1 is sectional view of the eyelid implant 10 of the present invention in use. The eyelid implant 10 is simple, safe and effective surgical approach for the treatment and functional rehabilitation of patients with deficient eyelid closure or ocular exposure, a complication often caused by facial nerve palsy. The conventional insertion of the eyelid weight implant is a reversible surgical procedure which takes advantage of the devices gravity to assist in satisfactory eyelid closure and partial recreation of a natural eye blink reflex. The device is surgically inserted above the eyeball in the upper eyelid, protecting against corneal exposure keratitis that could progress to a permanent visual loss. The weight eyelid implant of the present invention achieves good medical and cosmetic results in treating temporary and permanent facial paralysis in patients worldwide.

Figure 5:
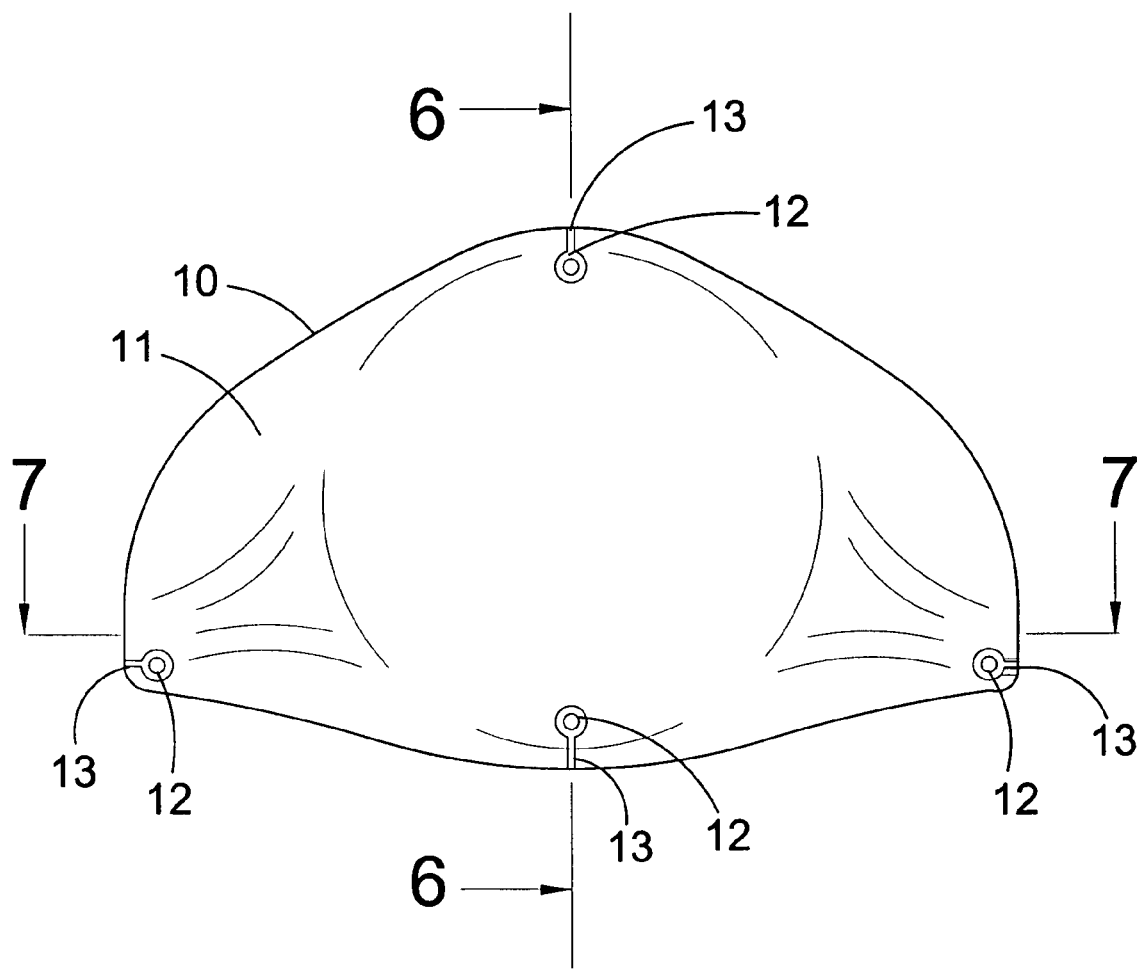
FIG. 5 is a front view of the eyelid implant of the present invention.

The eyelid implant 10 includes a main body 11. The main body 11 is formed from a non-reactive metal. Preferably, the main body is formed from gold. However, any non-reactive metal may be used to form the eyelid implant as long as the metal is able to form an eyelid weight having a desired size and weight while not causing a negative reaction with the user when implanted in the eyelid. As seen in FIG. 5, the main body 11 of the eyelid implant 10 has a plurality of suture holes 12. Each respective suture hole 12 extends through the main body 11 of the implant 10. The main body 11 of the eyelid implant 10 also contains a plurality of suture channels 16 positioned adjacent to a respective suture hole 12. Each suture channel 16 is carved into the top side 9 of the main body 11 and positioned adjacent to each suture hole 12. The shape and size of each suture channel 13 may be of any dimensions and shape able to retain the suture therein upon securing of the eyelid implant within the eyelid of the user's eye. The suture channels 13 preferably have a depth substantially equivalent to 400 microns. However, the suture channels 13 may be of any depth able to provide a recess for receiving a suture knot while losing off the suture hole 12 and not extending completely through the main body 11. The main body 11 of the eyelid weight 10 of the present invention is shown in cross section having the shape of a curved tear drop wherein a head end has a diameter larger than the diameter of a tail end. The shape of the implant 10 is shown within the enlarged circle. The larger diameter of the bottom end of the implant causes a gravity point indicated by the numeral 14 to be lower and central within the body 11. The gravity point 14 being positioned as shown in FIG. 1 allows gravity to effectively use the weight of the implant 10 to assist in closing of the eyelid. Additionally, the curved teardrop shape allows for a more natural fit against the eye itself as will be described below.

FIG. 1 shows a cross-section of an eye of a person having the eyelid weight 10 of the present invention implanted in an eyelid thereof. The eye is formed of a vitreous body 18 that is substantially circular. A first end of the vitreous body 18 has a depression wherein the lens 20 is positioned between the vitreous body 18 and the iris 22. The pupil 24 is positioned between at substantially a midpoint of the iris 22 and lens 20 and on a side of the lens opposite the vitreous body 18. The eye further includes the anterior chamber 28 and the posterior chamber 30. The anterior chamber 28 is positioned between the cornea 26 and the pupil 24. The conjunctiva 32 is positioned on a side of the cornea opposite the anterior chamber 28 and directly comes into contact with the upper eyelid 15 and the lower eyelid 38.

FIG. 1 shows the upper eyelid 15 having the implant 10 positioned therein. The curved teardrop shape of the body 11 of the implant 10 further enhances the ability to close the eyelid 15. As the gravity point 14 is positioned in a lower central portion of the body 11, the force of gravity causes the upper eyelid 15 to close over the conjunctiva 32. Furthermore, as the shape of the body 11 is curved, when the implant 10 passes over the curved shape of the conjunctiva, the result is a more natural and comfortable fit for the user having the implant 10 positioned therein. Additionally, the curved teardrop shape of the body 11 produces a more natural looking upper eyelid 15 and thus functions as a cosmetic treatment as well.

Figure 2:
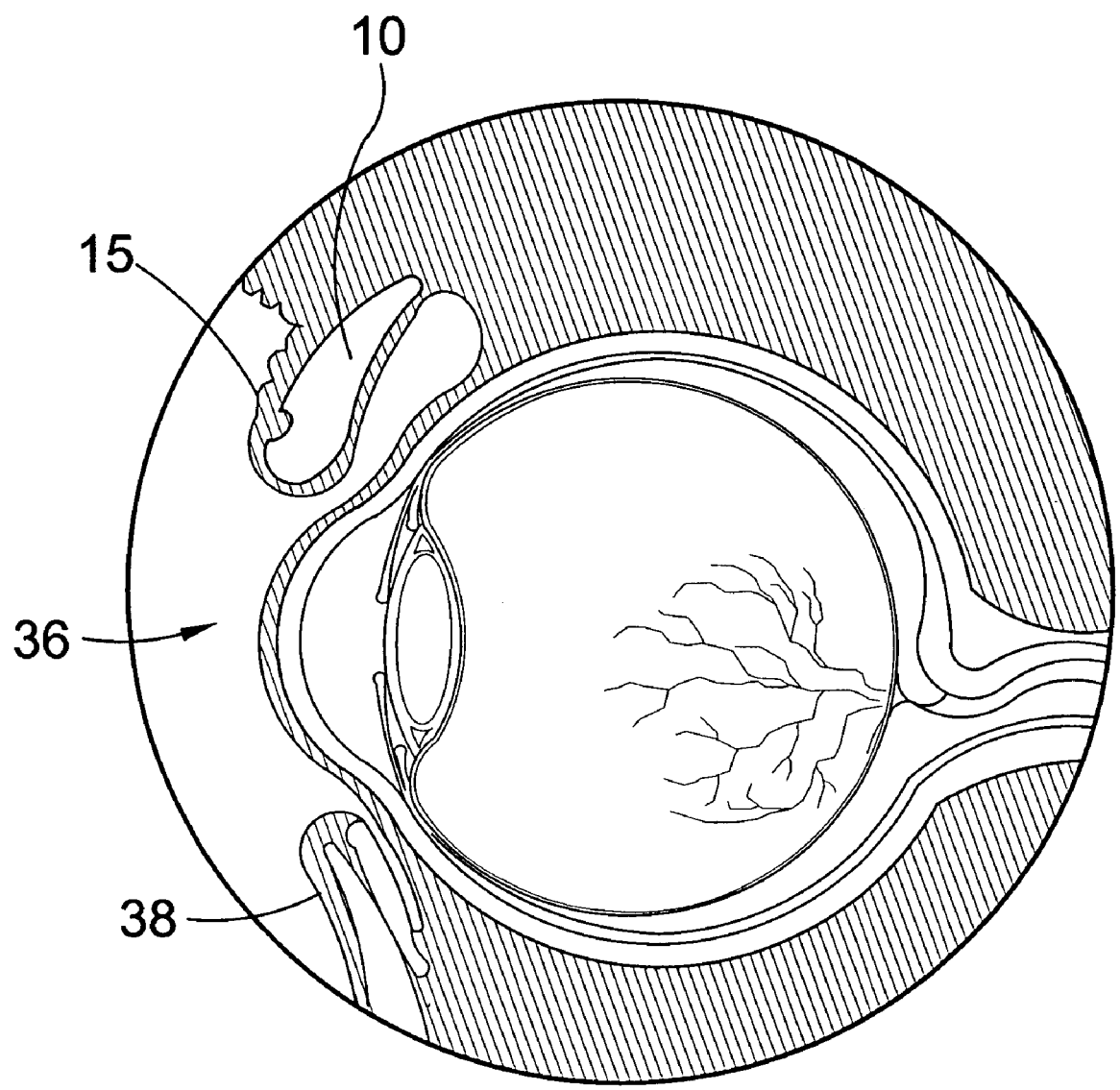
FIG. 2 is a sectional view of the eyelid implant of the present invention with the eyelid in the open position.

FIG. 2 is a sectional view of the eyelid implant of the present invention with the eyelid in the open position. The eyelid implant 10 includes a main body 11. The main body 11 is formed from a non-reactive metal. Preferably, the main body is formed from gold. However, any non-reactive metal may be used to form the eyelid implant as long as the metal is able to form an eyelid weight having a desired size and weight while not causing a negative reaction with the user when implanted in the eyelid. As seen in FIG. 5, the main body 11 of the eyelid implant 10 has a plurality of suture holes 12. Each respective suture hole 12 extends through the main body 11 of the implant 10. The main body 11 of the eyelid implant 10 also contains a plurality of suture channels 16 positioned adjacent to a respective suture hole 12. Each suture channel 16 is carved into the top side 9 of the main body 11 and positioned adjacent to each suture hole 12. The shape and size of each suture channel 13 may be of any dimensions and shape able to retain the suture therein upon securing of the eyelid implant within the eyelid of the user's eye. The suture channels 13 preferably have a depth substantially equivalent to 400 microns. However, the suture channels 13 may be of any depth able to provide a recess for receiving a suture knot while losing off the suture hole 12 and not extending completely through the main body 11. The main body 11 of the eyelid weight 10 of the present invention is shown in cross section having the shape of a curved tear drop wherein a head end has a diameter larger than the diameter of a tail end. The shape of the implant 10 is shown within the enlarged circle. The larger diameter of the bottom end of the implant causes a gravity point indicated by the numeral 14 to be lower and central within the body 11. The gravity point 14 being positioned as shown in FIG. 1 allows gravity to effectively use the weight of the implant 10 to assist in closing of the eyelid.

The eyelid weight 10 of the present invention has a shape substantially similar to a drop of water in cross section. When implanted, the weight is placed at the front eyelid 15 edge near the surface of the eyeball. When the eyelid 15 is closed, the implant 10 moves forward and down in an arc. The center of gravity 14 of the water-drop shaped moves outward and down, thereby maintaining more of the gravitational weight out and away from the body than is possible with conventional lid weight designs. The teardrop shape efficiently maximizes the weight to pull the eyelid closed. The head of the body 11 has a diameter larger than a diameter of the tail of the body 11, which is dynamically thin and lies unobtrusively above the eyeball. As shown in FIG. 2, the eyelids 15 and 38 are maintained in an open position.

Figure 3:
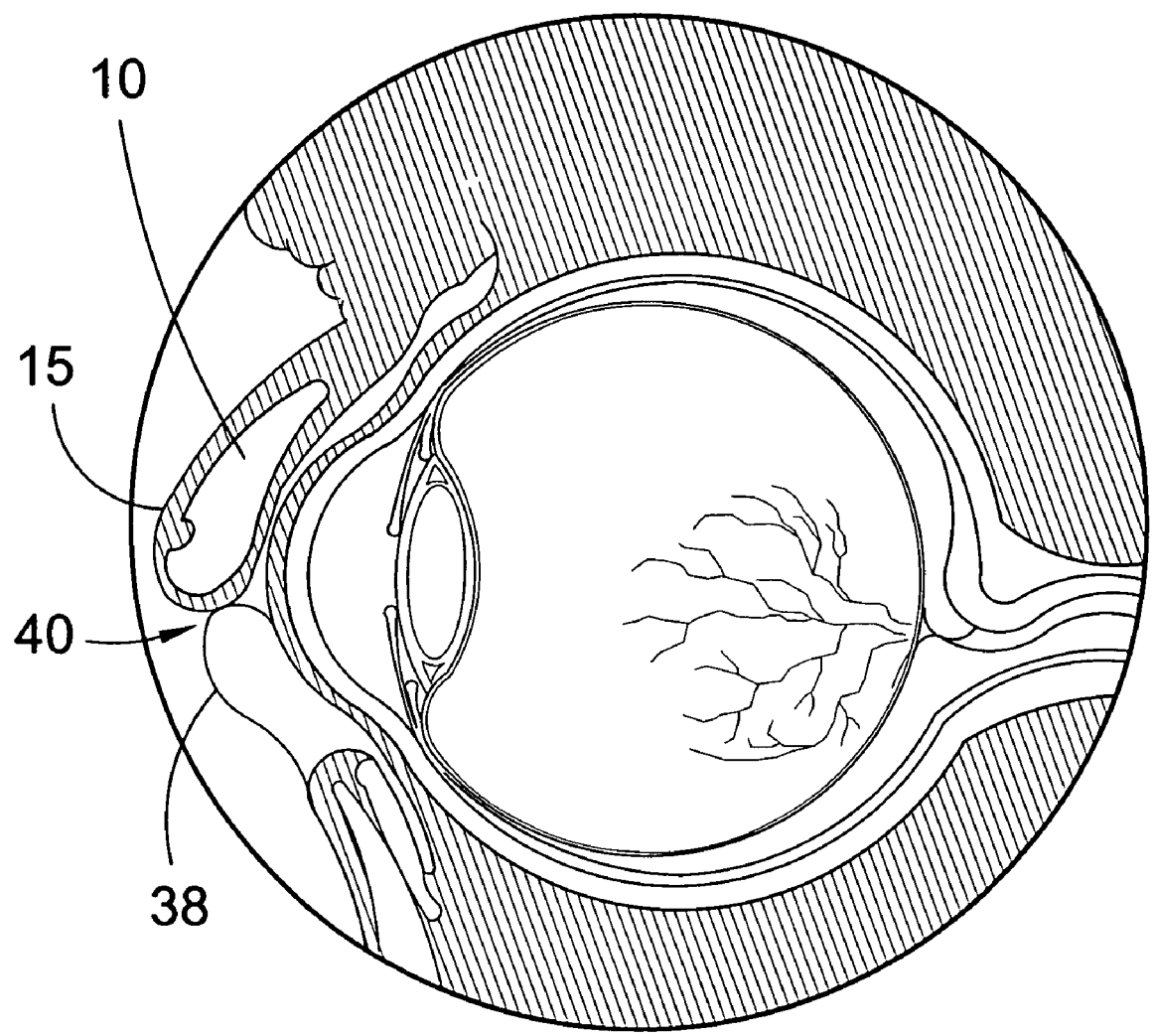
FIG. 3 is a sectional view of the eyelid implant of the present invention with the eyelid in the closed position.

FIG. 3 is a sectional view of the eyelid implant of the present invention with the eyelid in the closed position. The eyelid implant 10 includes a main body 11. The main body 11 is formed from a non-reactive metal. Preferably, the main body is formed from gold. However, any non-reactive metal may be used to form the eyelid implant as long as the metal is able to form an eyelid weight having a desired size and weight while not causing a negative reaction with the user when implanted in the eyelid. As seen in FIG. 5, the main body 11 of the eyelid implant 10 has a plurality of suture holes 12. Each respective suture hole 12 extends through the main body 11 of the implant 10. The main body 11 of the eyelid implant 10 also contains a plurality of suture channels 16 positioned adjacent to a respective suture hole 12. Each suture channel 16 is carved into the top side 9 of the main body 11 and positioned adjacent to each suture hole 12. The shape and size of each suture channel 13 may be of any dimensions and shape able to retain the suture therein upon securing of the eyelid implant within the eyelid of the user's eye. The suture channels 13 preferably have a depth substantially equivalent to 400 microns. However, the suture channels 13 may be of any depth able to provide a recess for receiving a suture knot while losing off the suture hole 12 and not extending completely through the main body 11. The main body 11 of the eyelid weight 10 of the present invention is shown in cross section having the shape of a curved tear drop wherein a head end has a diameter larger than the diameter of a tail end. The shape of the implant 10 is shown within the enlarged circle. The larger diameter of the bottom end of the implant causes a gravity point indicated by the numeral 14 to be lower and central within the body 11. The gravity point 14 being positioned as shown in FIG. 1 allows gravity to effectively use the weight of the implant 10 to assist in closing of the eyelid.

As shown in FIG. 3, the eyelid 15 of the user is in a closed position. The teardrop shape takes maximum advantage of gravity to pull the eyelid closed. The front of the device is much thicker than its tail, which is dynamically thin and lies unobtrusively above the eyeball and achieves a cosmetically better result. The fine tapered tail portion becomes gradually thinner as it follows the curvature of the eyeball from center to top.

Figure 4:
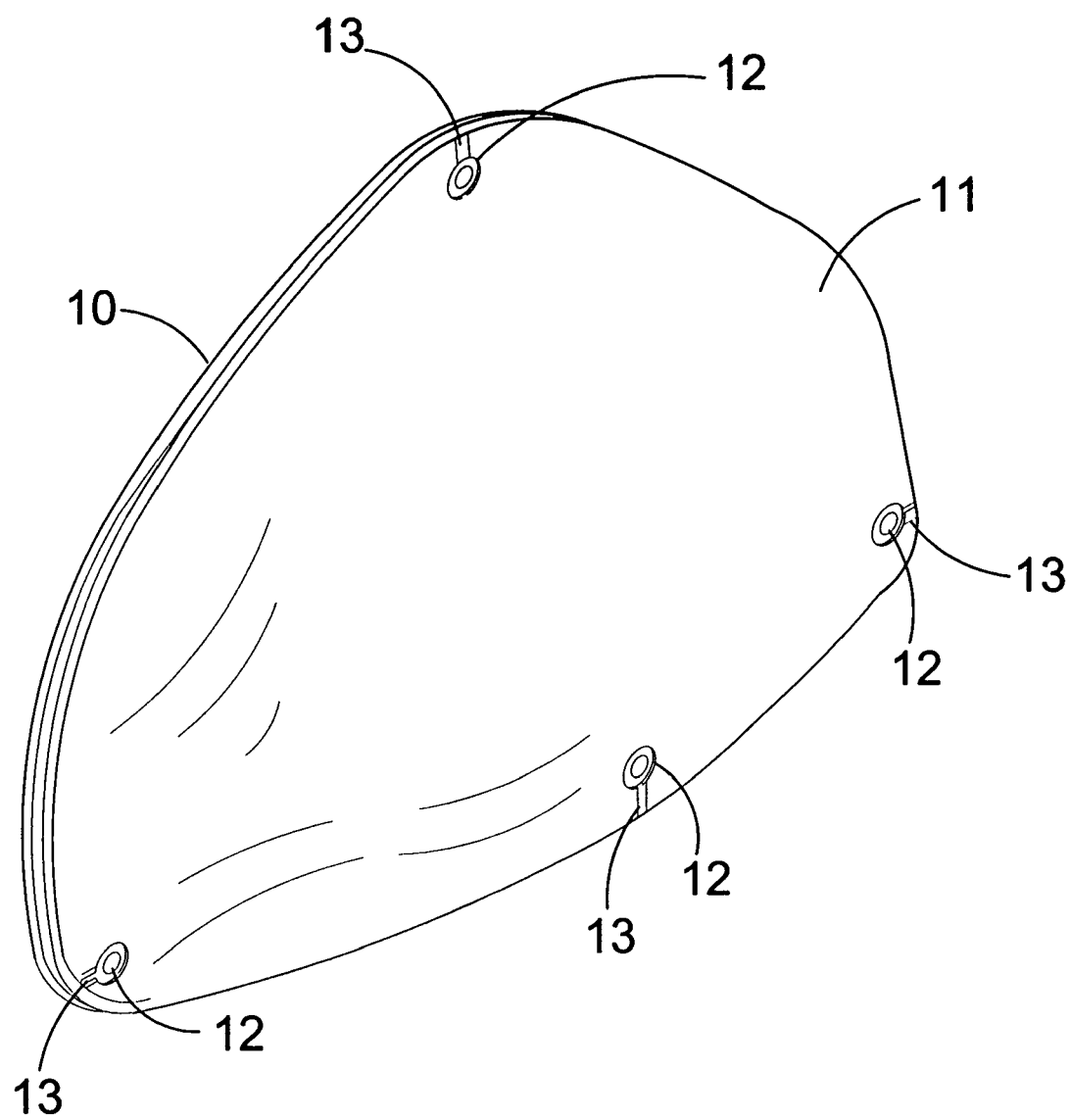
FIG. 4 is a perspective view of the eyelid implant of the present invention.

FIG. 4 is a perspective view of the eyelid implant of the present invention. The eyelid implant 10 includes a main body 11. The main body 11 is formed from a non-reactive metal. Preferably, the main body is formed from gold. However, any non-reactive metal may be used to form the eyelid implant as long as the metal is able to form an eyelid weight having a desired size and weight while not causing a negative reaction with the user when implanted in the eyelid. As seen in FIG. 5, the main body 11 of the eyelid implant 10 has a plurality of suture holes 12. Each respective suture hole 12 extends through the main body 11 of the implant 10. The main body 11 of the eyelid implant 10 also contains a plurality of suture channels 16 positioned adjacent to a respective suture hole 12. Each suture channel 16 is carved into the top side 9 of the main body 11 and positioned adjacent to each suture hole 12. The shape and size of each suture channel 13 may be of any dimensions and shape able to retain the suture therein upon securing of the eyelid implant within the eyelid of the user's eye. The suture channels 13 preferably have a depth substantially equivalent to 400 microns. However, the suture channels 13 may be of any depth able to provide a recess for receiving a suture knot while losing off the suture hole 12 and not extending completely through the main body 11. The main body 11 of the eyelid weight 10 of the present invention is shown in cross section having the shape of a curved tear drop wherein a head end has a diameter larger than the diameter of a tail end. The shape of the implant 10 is shown within the enlarged circle. The larger diameter of the bottom end of the implant causes a gravity point indicated by the numeral 14 to be lower and central within the body 11. The gravity point 14 being positioned as shown in FIG. 1 allows gravity to effectively use the weight of the implant 10 to assist in closing of the eyelid.

FIG. 5 is a front view of the eyelid implant of the present invention. The eyelid implant 10 includes a main body 11. The main body 11 is formed from a non-reactive metal. Preferably, the main body is formed from gold. However, any non-reactive metal may be used to form the eyelid implant as long as the metal is able to form an eyelid weight having a desired size and weight while not causing a negative reaction with the user when implanted in the eyelid. As seen in FIG. 5, the main body 111 of the eyelid implant 10 has a plurality of suture holes 12. Each respective suture hole 12 extends through the main body 11 of the implant 10. The main body 11 of the eyelid implant 10 also contains a plurality of suture channels 16 positioned adjacent to a respective suture hole 12. Each suture channel 16 is carved into the top side 9 of the main body 11 and positioned adjacent to each suture hole 12. The shape and size of each suture channel 13 may be of any dimensions and shape able to retain the suture therein upon securing of the eyelid implant within the eyelid of the user's eye. The suture channels 13 preferably have a depth substantially equivalent to 400 microns. However, the suture channels 13 may be of any depth able to provide a recess for receiving a suture knot while losing off the suture hole 12 and not extending completely through the main body 11. The main body 11 of the eyelid weight 10 of the present invention is shown in cross section having the shape of a curved tear drop wherein a head end has a diameter larger than the diameter of a tail end. The shape of the implant 10 is shown within the enlarged circle. The larger diameter of the bottom end of the implant causes a gravity point indicated by the numeral 14 to be lower and central within the body 11. The gravity point 14 being positioned as shown in FIG. 1 allows gravity to effectively use the weight of the implant 10 to assist in closing of the eyelid.

Figure 6:
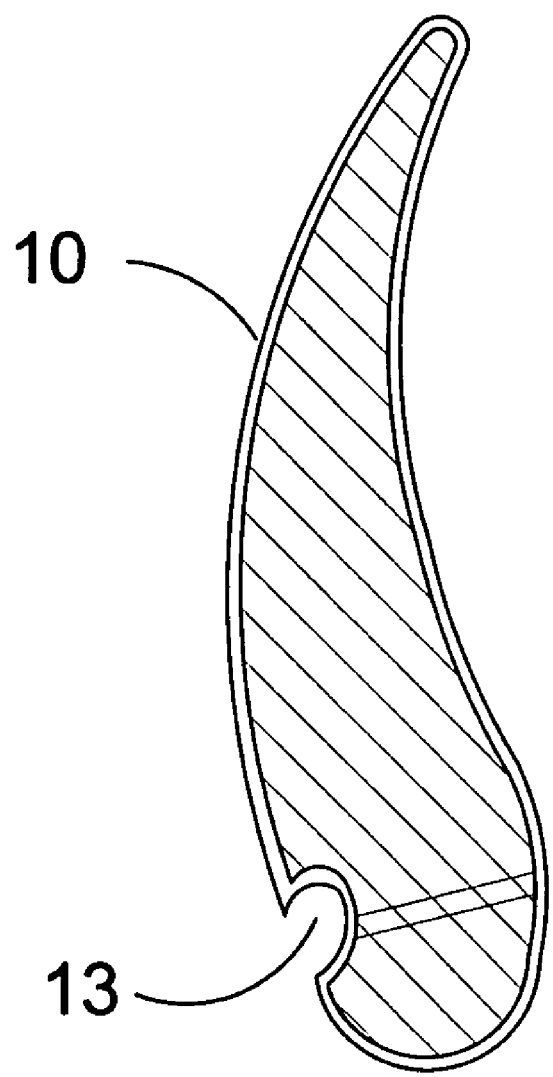
FIG. 6 is a cross-sectional side view of the eyelid implant of the present invention taken along line 5—5 in FIG. 5.

FIG. 6 is a cross-sectional side view of the eyelid implant of the present invention taken along line 5—5 in FIG. 5. The eyelid implant 10 includes a main body 11. The main body 11 is formed from a non-reactive metal. Preferably, the main body is formed from gold. However, any non-reactive metal may be used to form the eyelid implant as long as the metal is able to form an eyelid weight having a desired size and weight while not causing a negative reaction with the user when implanted in the eyelid. As seen in FIG. 5, the main body 11 of the eyelid implant 10 has a plurality of suture holes 12. Each respective suture hole 12 extends through the main body 11 of the implant 10. The main body 11 of the eyelid implant 10 also contains a plurality of suture channels 16 positioned adjacent to a respective suture hole 12. Each suture channel 16 is carved into the top side 9 of the main body 11 and positioned adjacent to each suture hole 12. The shape and size of each suture channel 13 may be of any dimensions and shape able to retain the suture therein upon securing of the eyelid implant within the eyelid of the user's eye. The suture channels 13 preferably have a depth substantially equivalent to 400 microns. However, the suture channels 13 may be of any depth able to provide a recess for receiving a suture knot while losing off the suture hole 12 and not extending completely through the main body 11. The main body 11 of the eyelid weight 10 of the present invention is shown in cross section having the shape of a curved tear drop wherein a head end has a diameter larger than the diameter of a tail end. The shape of the implant 10 is shown within the enlarged circle. The larger diameter of the bottom end of the implant causes a gravity point indicated by the numeral 14 to be lower and central within the body 11. The gravity point 14 being positioned as shown in FIG. 1 allows gravity to effectively use the weight of the implant 10 to assist in closing of the eyelid.

The eyelid implant 10 has a shape substantially similar to a drop of water. When implanted, the weight is placed at the front eyelid edge near the surface of the eyeball. When the upper eyelid 15 is closed, the implant 10 moves forward and down in an arc. The eyelid weight's 10 center of gravity 15 moves outward and down thereby causing the eyelid 15 to close more readily. The teardrop shape takes maximum advantage of the weight in order to pull the eyelid closed.

Figure 7:
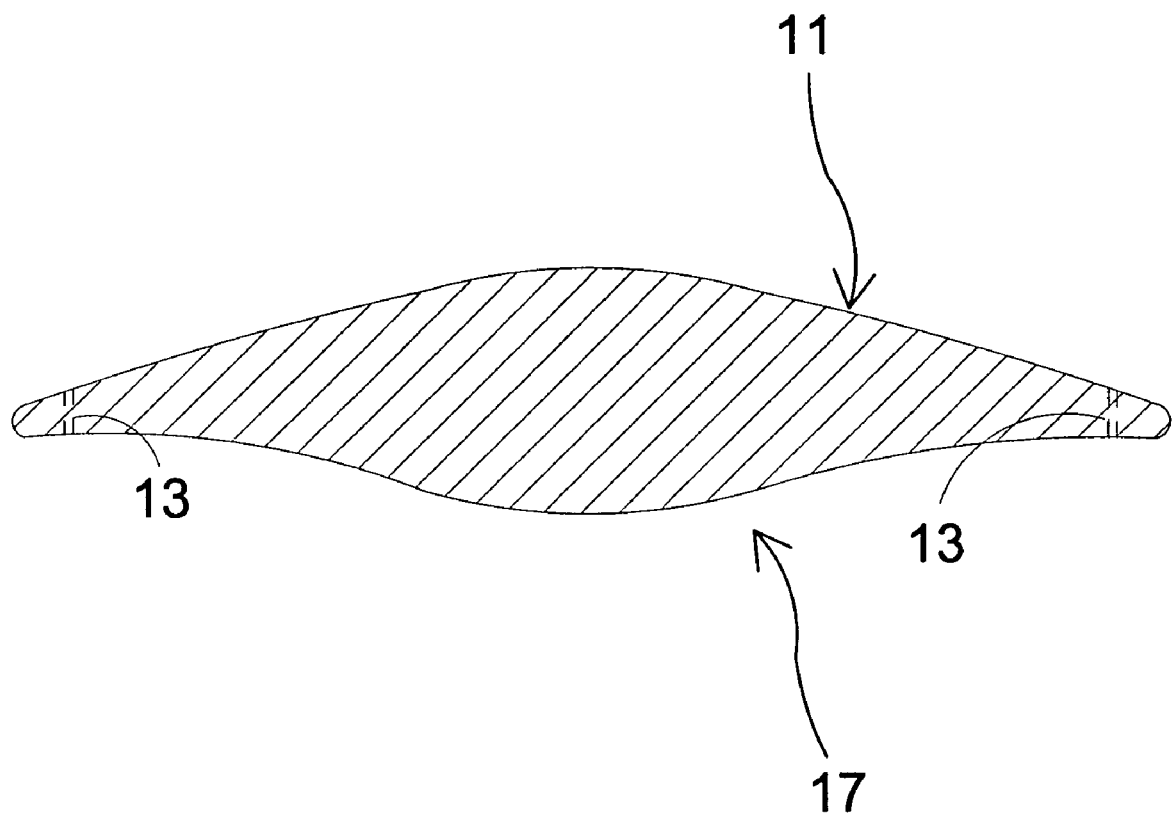
FIG. 7 is a bottom horizontal view of the eyelid implant of the present invention taken along the line 7—7 in FIG. 5.

FIG. 7 is a bottom horizontal view of the eyelid implant of the present invention taken along the line 7—7 in FIG. 5. The eyelid implant 10 includes a main body 11. The main body 11 is formed from a non-reactive metal. Preferably, the main body is formed from gold. However, any non-reactive metal may be used to form the eyelid implant as long as the metal is able to form an eyelid weight having a desired size and weight while not causing a negative reaction with the user when implanted in the eyelid. As seen in FIG. 5, the main body 11 of the eyelid implant 10 has a plurality of suture holes 12. Each respective suture hole 12 extends through the main body 11 of the implant 10. The main body 11 of the eyelid implant 10 also contains a plurality of suture channels 16 positioned adjacent to a respective suture hole 12. Each suture channel 16 is carved into the top side 9 of the main body 11 and positioned adjacent to each suture hole 12. The shape and size of each suture channel 13 may be of any dimensions and shape able to retain the suture therein upon securing of the eyelid implant within the eyelid of the user's eye. The suture channels 13 preferably have a depth substantially equivalent to 400 microns. However, the suture channels 13 may be of any depth able to provide a recess for receiving a suture knot while losing off the suture hole 12 and not extending completely through the main body 11. The main body 11 of the eyelid weight 10 of the present invention is shown in cross section having the shape of a curved tear drop wherein a head end has a diameter larger than the diameter of a tail end. The shape of the implant 10 is shown within the enlarged circle. The larger diameter of the bottom end of the implant causes a gravity point indicated by the numeral 14 to be lower and central within the body 11. The gravity point 14 being positioned as shown in FIG. 1 allows gravity to effectively use the weight of the implant 10 to assist in closing of the eyelid.

From the above description it can be seen that the eyelid implant 10 of the present invention is able to overcome the shortcomings of prior art devices by providing an eyelid implant that having a shape substantially similar to a drop of water thereby producing a center of gravity which maximizes the weight of the implant for more efficient and effective closing of the eyelid.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

The invention claimed is:

1. An eyelid implant comprising:
    a) a curved main body shaped to conform substantially to a cornea and an eyeball of a user and having in a cross section a water-drop shape with an enlarged head end and a narrowed tail end and a center of gravity of said main body being at substantially a center point of said enlarged head end, a diameter of said head end being substantially greater than a diameter of said tail end;
    b) at least one suture hole extending completely through said main body; and
    c) at least one suture channel, extending partially through said main body to a predetermined depth, wherein a suture is passed through said at least one suture hole for securing said eyelid implant to an eyelid of a user and said implant causes said eyelid to close.

2. The eyelid implant as recited in claim 1, wherein said main body is formed from a non-reactive metal.

3. The eyelid implant as recited in claim 2, wherein said non-reactive metal is gold.

4. The eyelid implant as recited in claim 1, wherein said main body is formed substantially as an arced water drop.

5. The eyelid implant as recited in claim 4, wherein an arc of a rear side of said main body is substantially equal to the arc of the eyeball thereby allowing easy passage thereover when the eyelid is in the closed position.

6. The eyelid implant as recited in claim 1, wherein said head end is adapted to be positioned at a front end of an eyelid thereby causing the eyelid to move in outward and downward direction.

7. The eyelid implant as recited in claim 1, wherein said main body in a front view thereof is substantially triangular in shape with all corners rounded and all sides being curved.

8. The eyelid implant as recited in claim 7, wherein a suture hole is located adjacent each corner of said main body, one of said sides having a suture hole located at a midpoint.

9. The eyelid implant as recited in claim 1, wherein said at least one suture channel is formed from a base, a first side and a second side, said first side being parallel to said second side, said first and second sides extending perpendicular to said base.

10. The eyelid implant as recited in claim 9, wherein said suture channel extends between an edge of said main body to said suture hole.

11. The eyelid implant as recited in claim 10, wherein said suture channel extends through said main body to a depth of substantially 400 microns for the purpose of securing the suture and to prevent movement of the implant.

* * * * *